United States Patent
Baksmaty et al.

(10) Patent No.: US 12,111,305 B2
(45) Date of Patent: Oct. 8, 2024

(54) METHOD FOR DETERMINING SUBSURFACE HYDROCARBON FLUID PROPERTIES OF RESERVOIRED HYDROCARBONS

(71) Applicant: SHELL OIL COMPANY, Houston, TX (US)

(72) Inventors: Leslie Owuraku Baksmaty, Houston, TX (US); Ram Ratan Ratnakar, Houston, TX (US); Birol Dindoruk, Houston, TX (US)

(73) Assignee: SHELL USA, INC., Houston, TX (US)

( * ) Notice: Subject to any disclaimer, the term of this patent is extended or adjusted under 35 U.S.C. 154(b) by 367 days.

(21) Appl. No.: 17/611,349

(22) PCT Filed: Jun. 12, 2020

(86) PCT No.: PCT/US2020/037412
§ 371 (c)(1),
(2) Date: Nov. 15, 2021

(87) PCT Pub. No.: WO2020/252246
PCT Pub. Date: Dec. 17, 2020

(65) Prior Publication Data
US 2022/0205970 A1 Jun. 30, 2022

Related U.S. Application Data

(60) Provisional application No. 62/860,847, filed on Jun. 13, 2019.

(30) Foreign Application Priority Data

Jul. 9, 2019 (EP) .................................. 19185152

(51) Int. Cl.
| G01N 33/24 | (2006.01) |
| E21B 49/08 | (2006.01) |
| G01V 1/38 | (2006.01) |

(52) U.S. Cl.
CPC .......... *G01N 33/241* (2013.01); *E21B 49/08* (2013.01); *G01V 1/3808* (2013.01)

(58) Field of Classification Search
CPC ............ G01V 1/3808; G01N 33/2823; G01N 33/241; E21B 49/08; E21B 49/00
See application file for complete search history.

(56) References Cited

U.S. PATENT DOCUMENTS 7,318,343 B2 * 1/2008 Coenen .................... E21B 49/08
73/152.01
8,316,934 B2 * 11/2012 Pietrobon ................ E21B 47/11
166/250.15

(Continued)

OTHER PUBLICATIONS

International Search Report and Written Opinion received for PCT Patent Application No. PCT/US2020/037412, mailed on Sep. 9, 2020, 10 pages.

(Continued)

*Primary Examiner* — An H Do
(74) *Attorney, Agent, or Firm* — SHELL USA, INC.

(57) ABSTRACT

A method for determining subsurface hydrocarbon fluid properties of reservoired hydrocarbons having a hydrocarbon seep involves locating a hydrocarbon seep at a seabed location where hydrocarbon is actively flowing out of the seabed. A sample of hydrocarbons is collected from the hydrocarbon seep. Physical, transport and/or thermodynamic fluid properties of reservoired hydrocarbons are determined from the sample of hydrocarbons.

9 Claims, 2 Drawing Sheets

(56) References Cited

U.S. PATENT DOCUMENTS

| | | | |
|---|---|---|---|
| 9,612,231 | B2 | 4/2017 | Pottorf et al. |
| 10,527,601 | B2 * | 1/2020 | Dreyfus ................ G01V 9/007 |
| 2006/0154306 | A1 | 7/2006 | Kotlar et al. |
| 2008/0147326 | A1 | 6/2008 | Ellis |
| 2014/0250999 | A1 | 9/2014 | Lawson et al. |
| 2015/0127313 | A1 | 5/2015 | Lawson et al. |
| 2016/0341038 | A1 | 11/2016 | AbuAli et al. |
| 2018/0321215 | A1 | 11/2018 | Peterson et al. |

OTHER PUBLICATIONS

Mau et al., "Compositional Variability and Air-sea Flux of Ethane and Propane in the Plume of a Large, Marine Seep Field Near Coal Oil Point", Geo—Marine Letters, An International Journal of Marine Geology, vol. 30, Issue No. 3-4, Feb. 20, 2010, pp. 367-378, XP019845758.

Pape et al., "Gas Hydrates in Shallow Deposits of the Amsterdam Mud Volcano, Anaximander Mountains, Northeastern Mediterranean Sea", Geo—Marine Letters, An International Journal of Marine Geology, vol. 30, Issue No. 3-4, Mar. 16, 2010, pp. 187-206, XP019845769.

Sassen et al., "Massive Vein-filling Gas Hydrate: Relation to Ongoing Gas Migration From the Deep Subsurface in the Gulf of Mexico", Marine and Petroleum Geology, vol. 18, 2001, pp. 551-560.

Kennicutt et al., "Leakage of Deep, Reservoired Petroleum to the Near Surface on the Gulf of Mexico Continental Slope", Marine Chemistry, vol. 24, 1988, pp. 39-59.

\* cited by examiner

METHOD FOR DETERMINING SUBSURFACE HYDROCARBON FLUID PROPERTIES OF RESERVOIRED HYDROCARBONS

CROSS REFERENCE TO RELATED APPLICATIONS

This is a National stage application of International application No. PCT/US2020/037412, filed Jun. 12, 2020, which claims priority of U.S. application No. 62/860,847, filed 13 Jun. 2019 and EP application Ser. No. 19/185,152.6 filed 9 Jul. 2019, which is incorporated herein by reference in its entirety.

FIELD OF THE INVENTION

The present invention relates to the field of determining the fluid properties of reservoired hydrocarbons from a hydrocarbon seep.

BACKGROUND OF THE INVENTION

Exploration for reservoired hydrocarbons in a marine environment is more costly and complex compared to many exploration endeavours on land. An important tool for improving the probability of success in discovering new oil reserves is detecting seeps, effectively leaks of hydrocarbons from reservoirs. However, not all seeps are indicative of reservoired hydrocarbons. In some instances, seeps are not connected to reservoired hydrocarbons.

A method for detecting hydrocarbon seepages into the sea is described in U.S. Pat. No. 9,612,231B2 (Pottorf et al., 4 Apr. 2017). The method starts with performing a remote sensing survey and analysing the remote sensing data from the remote sensing survey to determine the location of hydrocarbon seeps into the sea. The remote sensing survey may include performing one or more of ocean acoustic waveguide survey, water column seismic survey, active acoustic sensing survey, imagery and spectrometry of slicks and atmospheric gas plumes, passive acoustic sensing survey, magnetic and gravity surveys, optical sensing survey and thermal anomalies detection survey. These surveys include seismic and acoustic imaging of seeps in the water column, performed in ship-based marine vessels, using multibeam echo sounder and/or side-scan sonar.

In another member of the same patent family, US20140250999A1 (Lawson et al., 11 Sep. 2014) describes a method for reservoir surveillance. Samples of produced fluids are analysed for changes over time in noble gas and clumped isotope signatures. And in yet another member of the same family, US20150127313A1 (Lawson et al., 7 May 2015) describes a method for determining the presence and location of a subsurface hydrocarbon accumulation by comparing a clumped isotopic signature with an expected or theoretical concentration of isotopologues of a hydrocarbon species calculated by molecular modelling. According to Lawson et al, the "differentiation between direct seepage from a source rock from the leakage of hydrocarbons from a subsurface accumulation requires consideration of the clumped isotopic signatures that may result from the two models of seepage. Hydrocarbons that have migrated directly from a source rock may either (i) retain a stochastic clumped isotope signature given insufficient time for a thermal contribution to the "clumping" of multiply substituted isotopologues, or (ii) display an inconsistent clumped isotope signature that arises as a result of the variability in the rate of isotope exchange of individual isotopologues. In contrast, hydrocarbons that derive from a subsurface accumulation will retain a clumped isotope signature that more consistently reflects the temperature at which they were stored in the subsurface." The solution presented in Lawson et al is to calculate a theoretical clumped isotopic signature for each isotopologue using molecular modelling.

Kennicutt et al ("Leakage of deep, reservoired petroleum to the near surface on the Gulf of Mexico continental slope," *Marine Chemistry* 24:39-59; 1988) discusses the link between natural seepage in a deepwater marine setting and the formation of sea slicks and tar balls. Analysis of the gaseous and liquid hydrocarbons show that gas migrates to shallow sediments with little or no isotopic fractionation. Table 1 illustrates that carbon isotopic compositions are essentially unchanged after migration from reservoirs at depths >2000 m. In contrast, Kennicutt et al found that near-surface hydrocarbon liquids were depleted in aliphatics, 4-ring or larger aromatics, naphthalene, C1-naphthalenes and C2-naphthalenes as compared to reservoired fluids.

Sassen et al ("Massive vein-filling gas hydrate: relation to ongoing gas migration from the deep subsurface in the Gulf of Mexico," *Marine and Petroleum Geology* 18:551-560; 2001) show correlation of isotopic properties of C1-C5 hydrocarbons from reservoirs, gas vents and gas hydrates for the same seeps in Kennicutt et al (1988).

There is a need for methods to determine the subsurface fluid properties of reservoired hydrocarbons from a seep.

SUMMARY OF THE INVENTION

A method for determining subsurface hydrocarbon fluid properties of reservoired hydrocarbons having a hydrocarbon seep, the method comprising the steps of: (a) locating a hydrocarbon seep at a seabed location where hydrocarbon is actively flowing out of the seabed; (b) collecting a sample of hydrocarbons from the hydrocarbon seep; and (c) determining the fluid properties of reservoired hydrocarbons from the sample of hydrocarbons, the fluid properties selected from the group consisting of physical, transport and thermodynamic properties.

BRIEF DESCRIPTION OF THE DRAWINGS

The present invention will be better understood by referring to the following detailed description of preferred embodiments and the drawings referenced therein, in which.

DETAILED DESCRIPTION OF THE INVENTION

Figure 1:
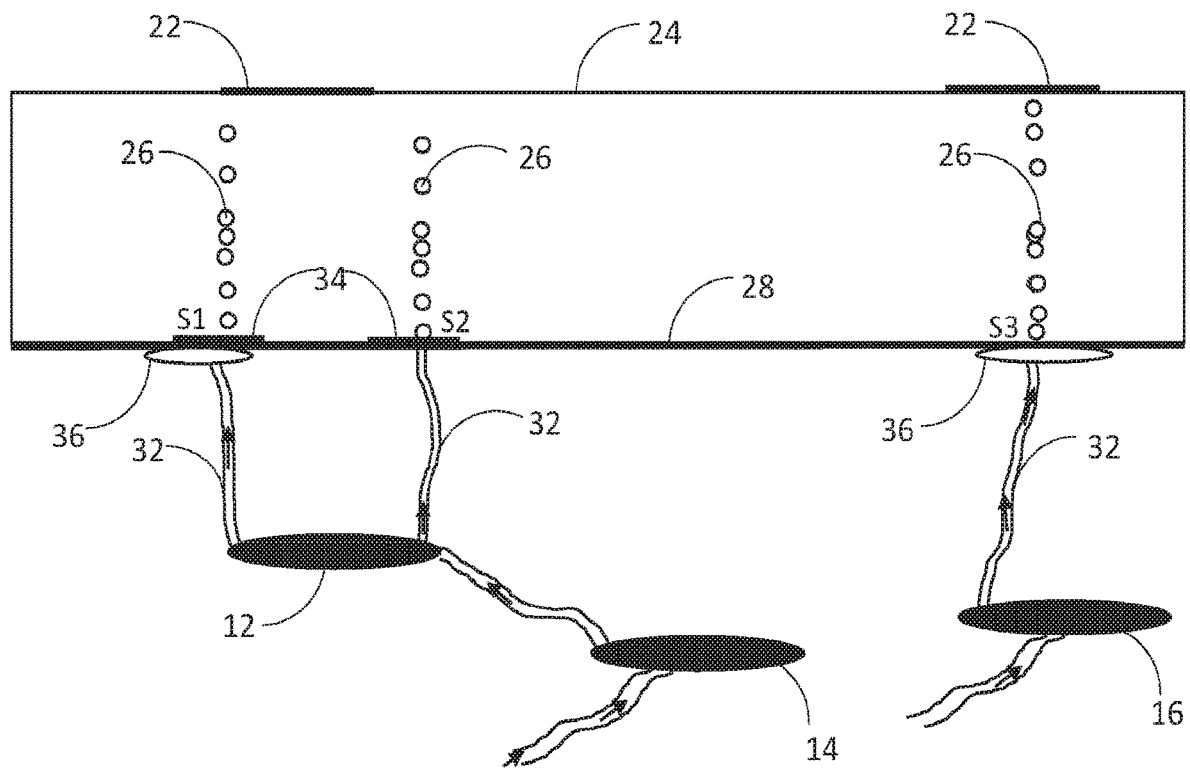
FIG. 1 illustrates different types of hydrocarbon seeps in a body of water.

In one embodiment, the present invention provides a method for determining the subsurface fluid properties of reservoired hydrocarbons having a hydrocarbon seep.

The method of the present invention involves determining physical, transport and/or thermodynamic fluid properties from a sample of hydrocarbons collected from an active hydrocarbon seep. Preferably, the fluid properties are determined by constructing a phase envelope from the sample of hydrocarbons.

More preferably the methods of the present invention involve determining at least two temporally spaced compositions from a hydrocarbon seep. By determining whether a variance between two temporally spaced compositions falls within a temporal tolerance, the method of the present invention determines that a steady state exists, thereby suggesting that the hydrocarbon seep is more likely indicative of reservoired hydrocarbons, as opposed to a seep originating directly from a source rock. The temporally spaced compositions may be isotopic and/or molecular compositions.

The physical, transport and/or thermodynamic properties include, without limitation, viscosity, gas:oil ratio, dew point, bubble point, molecular composition, isotopic composition, API gravity and/or density.

"Reservoired hydrocarbons" as used herein means that the hydrocarbons are reservoired in an oil reservoir or a gas reservoir. A reservoir is an underground formation containing an individual and separate natural accumulation of producible hydrocarbons. An oil reservoir generally contains gas, oil and water, with oil being a major component. When gas accumulates independently of the oil, the reservoir is referred to as a gas reservoir, which may also contain some water and oil. A gas reservoir is a naturally occurring storage area of natural gas. In a condensate reservoir, hydrocarbons may exist as a gas, but when brought to the surface, the heavier hydrocarbons condense to a liquid.

A "seep" or "hydrocarbon seep" is an indicator of hydrocarbons escaping the subsurface to a seabed, often under low pressure or flow. The hydrocarbons may escape from a reservoir along geological layers, or through fractures and fissures in the rock. Hydrocarbon seeps may result in bubble plumes in a water column, production of gas hydrates on the seabed, and/or production of oil slicks on the surface of the sea. Seeps may also arise from hydrocarbons escaping source rock that are not connected to a reservoir.

As used herein, "actively flowing" means that there is mass transfer of hydrocarbons. Indicators of an actively flowing seep include, without limitation, a bubble plume, a distinct phase from surrounding water, intrusion of one fluid into another, non-diffusive transport, and an accumulation of gas hydrates or oil that increases with time. The term "bubbles" is used for vapour-filled bubbles, as well as liquid droplets. The bubbles may or may not be at least partially frozen. In the case of hydrocarbon-containing bubbles, the bubbles may be at least partially in the form of hydrocarbon hydrates, such as methane hydrates. For example, a bubble may have a hydrate shell around a hydrocarbon fluid. Accordingly, it will be understood by those skilled in the art that the bubble plume may be formed of liquid or gas depending on, for example, the depth of the water. Often, in a subsea hydrocarbon seep, $C_1$-$C_4$ components, which are typically gaseous at STP, are in liquid form at or near the seabed.

As used herein, "isotopes" refers to variants of a chemical element with different numbers of neutrons. For example, carbon has 15 known isotopes, from $^8C$ to $^{22}C$, of which $^{12}C$ and $^{13}C$ are stable isotopes. Hydrogen has three-naturally occurring isotopes-protium $^1H$ with zero neutrons, deuterium $^2H$ (or D) with one neutron and tritium $^3H$ with two neutrons. "Isotopologues" are molecules that have the same chemical composition but differ only in their isotopic composition. As an example, methane has ten stable isotopologues: $^{12}CH_4$, $^{13}CH_4$, $^{12}CH_3D$, $^{13}CH_3D$, $^{12}CH_2D_2$, $^{12}CH_2D_2$, $^{13}CH_2D_2$, $^{12}CHD_3$, $^{13}CHD_3$, $^{12}CD_4$ and $^{13}CD_4$. In this example, $^{12}CH_4$ is an unsubstituted isotopologue, $^{13}CH_4$ and $^{12}CH_3D$ are singly substituted isotopologues and $^{13}CH_3D$ and $^{12}CH_2D_2$ are doubly substituted isotopologues. Multiple-substituted isotopologues, for example $^{13}CH_3D$ and $^{12}CH_2D_2$, are termed "clumped isotopologues."

By "isotopic composition," we mean the relative amounts or distribution of individual isotopologues measured (in wt. or mol %).

By "molecular composition," we mean the relative amounts or distribution of individual molecules measured (in wt. or mol %). The molecular composition may be limited to hydrocarbons, for example C1-C7 hydrocarbons, or may also include non-hydrocarbons of interest.

As used herein, "steady state" means that the isotopic and/or molecular composition is stable with respect to time, within a predetermined tolerance.

Referring now to the drawing, FIG. 1 illustrates different types of hydrocarbon seeps from hydrocarbon reservoirs 12, 14, 16. Oil slicks 22 at the sea surface 24 or hydrocarbon streams 26, as a bubble plume and/or a distinct phase from surrounding water, at the sea surface 24 or seabed 28 may be indicative of a subsurface reservoir 12, 14, 16. Hydrocarbons from a hydrocarbon reservoir 12, 14, 16 migrate to the seabed 28 through fractures 32. At the seabed 28, microbial, especially bacterial, mats 34 and/or other sea life (not shown), such as tube worms and seep mussels, may accumulate around a seep location, S1, S2, S3. However, the microbial mats 34 may not necessarily be visible or present around an active seep S1, S2, S3. Furthermore, microbial mats 34 may form at other hydrocarbon sources (not shown) that do not originate from a hydrocarbon reservoir 12, 14, 16.

For simplicity, oil slicks 22 and hydrocarbon streams 26 are illustrated as being located directly above the seep S1, S2, S3. However, it will be understood by those skilled in the art that the oil slicks 22 and hydrocarbon streams 26 may drift with wave and/or motion and/or tidal forces at and/or below the sea surface 24 and may be some distance from the seep S1, S2, S3. FIG. 1 depicts gas accumulations 36 at or below the seabed 28. Typically, the gas accumulations 36 are associated with a reservoir 12, 14, 16. The gas accumulations 36 may be in the form of trapped gas and/or gas hydrates. For ease of discussion, the various elements in FIG. 1 are not to scale. For example, the gas accumulation 36 may be significantly smaller than the reservoir 12, 14, 16.

FIG. 1 illustrates one active seep S3 from hydrocarbon reservoir 16. FIG. 1 also shows a reservoir 14 that is connected to another reservoir 12. When reservoir 12 is well-mixed, the composition from seep S1 and seep S2 will be substantially similar. However, when reservoir 12 is partitioned, the composition from seep S1 and seep S2 may be different. Isotopic compositions from seep S1 and seep S2 are more likely to be substantially similar. The molecular composition from seep S1 may differ from seep S2 due to partitioning effects in reservoir 12 and/or gas accumulation 36.

Figure 2:
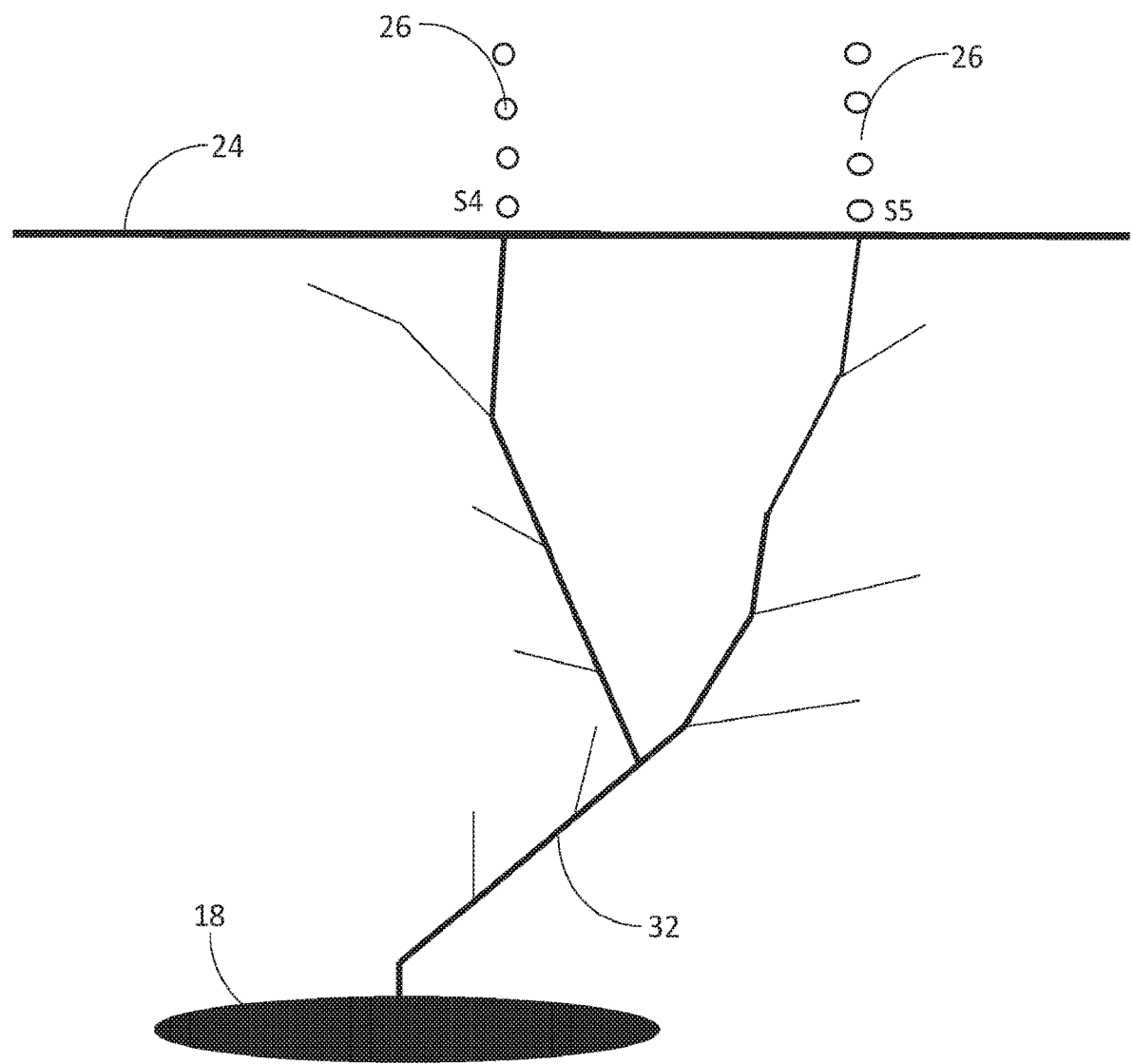
FIG. 2 illustrates a hydrocarbon reservoir with 2 active hydrocarbon seeps.

FIG. 2 illustrates an embodiment where seeps S4 and S5 originate from the same reservoir 18 from fracture 32, which later splits into two main fractures resulting in separate seeps S4 and S5. Isotopic and/or molecular compositions of hydrocarbon streams 26 are expected to be substantially similar for seeps S4 and S5. For ease of discussion, the various elements in FIG. 2 are not to scale.

In accordance with the present invention, a hydrocarbon seep S1, S2, S3, S4, S5 is first found at a seabed location where hydrocarbon is actively flowing out of the seabed 28. The hydrocarbon seep S1, S2, S3, S4, S5 may be detected for example, without limitation, by satellite, aircraft or watercraft detection and/or observation of hydrocarbon slicks 22 and/or hydrocarbon streams 26. The hydrocarbon seep S1, S2, S3, S4, S5 may also be located by planned or unplanned surveillance by an underwater vehicle.

Once located, at least two temporally spaced molecular and/or isotopic compositions of the hydrocarbon seep S1, S2, S3, S4, S5 are determined.

The molecular compositions are determined for example, without limitation, by gas chromatography-mass spectrometry (GC/MS), GC/GC/MS, and/or liquid chromatography. In another embodiment, analysis of samples may also be conducted. This may include, for example, without limitation, inductively coupled plasma mass spectrometry (ICP-MS) and ICP-optical emission spectroscopy. Gas chemistry analysis may also be conducted and may include isotope ratio-mass spectrometry and GC.

The isotopic compositions are determined, for example, without limitation, by mass spectroscopy, laser-based spectroscopy, and other methods/apparatus known to those skilled in the art. The isotopic compositions are determined, for example, without limitation, by mass spectroscopy, laser-based spectroscopy, and other methods/apparatus known to those skilled in the art. Preferably, the temporally spaced isotopic composition is defined by isotopic compositions of hydrocarbons selected from the group consisting of methane, ethane, propane, butane, and combinations thereof. More preferably, the temporally spaced isotopic composition is defined by isotopic compositions of hydrocarbons, such as, for example, without limitation, methane, ethane, propane, and/or butane, as well as isotopic compositions of non-hydrocarbons, such as, for example, without limitation, carbon dioxide and/or hydrogen sulphide.

Preferably, the compositions are determined by capturing and/or in-situ probing hydrocarbons from the hydrocarbon streams 26. For example, a sample of hydrocarbon stream 26 may be captured isobarically, so that the components of the sample remain unchanged when taken to a testing site, for example at sea level. Alternatively, compositions may be determined by underwater mass spectrometers, Raman spectroscopy, isotope probes, and the like.

Samples may be obtained, for example, by divers, underwater vehicles, including manned and unmanned submersibles, remotely operated underwater vehicles (ROV), autonomous underwater vehicles (AUV), and the like. Alternatively, or in combination, the compositions may be determined without the need for a physical sample, for example, by Raman spectroscopy or isotope probes, known to those skilled in the art.

Analysis of the samples may be determined in-situ and/or remotely. For example, some fluid properties may be determined in situ, while a detailed PVT analysis is preferably conducted remotely in a laboratory.

A camera may be used while collecting samples. In a preferred embodiment samples of hydrocarbon gas and hydrocarbon oil are taken from the same seep location. The gas and oil may be captured in the same sample container or may be independently captured. In the latter case, it may be particularly advantageous to use a camera to determine the volumetric flow rate. In this way, the gas and oil samples may be combined in the correct volumetric ratio for an analysis of the recombined sample.

The at least two temporally spaced compositions may be determined, for example, by compositions may be determined by samples and/or measurements taken 12 to 24 hours apart. The objective of temporal spacing is to account for periodicity, especially, for example, tidal forces, to assess whether a composition is at steady state. Accordingly, it is within the scope of the present invention to determine a composition at time $t_0$ and then determine a composition 1 day or week, for example, later, with or without an offset of 12 hours.

The at least two temporally spaced compositions of the hydrocarbon seep are analysed for relative amounts or distribution of certain or all isotopic and/or molecular components. Preferably, more than two temporally spaced isotopic and/or molecular compositions of the hydrocarbon seep are determined and analysed to improve resolution of the compositions.

Isotopic compositions are particularly useful for identifying the presence of reservoired hydrocarbons because they are indicative of the thermal maturity of the hydrocarbons in the reservoir. Furthermore, isotopic compositions are substantially unaffected by diffusivity as the hydrocarbon migrates to the seabed.

Molecular compositions are more susceptible to diffusivity effects. However, substantial consistency between temporally spaced molecular compositions is a strong indicator of the presence of reservoired hydrocarbons. Accordingly, in a preferred embodiment of the present invention, both isotopic and molecular compositions are determined.

Oil samples typically will have a strong relationship to the source of reservoired hydrocarbons. Gas samples are more sensitive to how the gas migrated to the seabed from the reservoir.

In a preferred embodiment, a base set of isotopologues and/or compounds are selected for comparing temporal and/or spatial variances between temporally spaced compositions.

Nonhydrocarbon gases, such as hydrogen sulphide and carbon dioxide, may be produced with or in addition to hydrocarbons. Preferably, the nonhydrocarbon gases are considered as part of the isotopic and/or molecular composition. More preferably, $CO_2$ is considered as part of the isotopic and/or molecular composition. The information about carbon dioxide can provide more insights into the reservoir characteristics.

The at least two temporally spaced compositions are then compared to determine a temporal variance between the compositions. When the temporal variance falls within a predetermined temporal tolerance, the hydrocarbon seep related to the at least two compositions is classified as being indicative of the presence of reservoired hydrocarbons. The value of the temporal tolerance will be dependent on a number of factors, including the compound and/or isotope/isotopologue being considered, the time difference between samples, tidal forces, and the like.

When a hydrocarbon seep is classified as being indicative of the presence of reservoired hydrocarbons, a unique identifier can be assigned to the reservoired hydrocarbons.

In one embodiment, the method involves locating a plurality of hydrocarbon seeps. At least two temporally spaced compositions are determined and when a temporal variance between the at least two temporally spaced compositions falls within a predetermined temporal tolerance, a hydrocarbon seep is classified as being indicative of the presence of reservoired hydrocarbons. A representative composition is then selected for each of the hydrocarbon seeps classified as being indicative of the presence of reservoired hydrocarbons. A spatial variance is determined between the representative compositions. When the spatial variance falls within a predetermined spatial tolerance, the same unique identifier is assigned to the reservoired hydrocarbons. In this way, independent hydrocarbon seeps can be identified as originating from the same or different reservoir.

While preferred embodiments of the present invention have been described, it should be understood that various changes, adaptations and modifications can be made therein within the scope of the invention(s) as claimed below.

The invention claimed is:

1. A method for determining the fluid properties of subsurface reservoired hydrocarbons having a hydrocarbon seep, the method comprising the steps of:
   a) locating a hydrocarbon seep at a seabed location where hydrocarbons are actively flowing out of the seabed;
   b) collecting a sample of hydrocarbons from the hydrocarbon seep;
   c) determining the fluid properties of subsurface reservoired hydrocarbons from the sample of hydrocarbons, the fluid properties selected from the group consisting of physical, transport and thermodynamic properties; and
   d) determining whether the seep is at a steady state, indicative of reservoired hydrocarbons, by
      (i) determining at least two temporally spaced compositions of the hydrocarbon seep, the at least temporally spaced compositions selected from the group consisting of isotopic compositions, molecular compositions, and combinations thereof,
      (ii) determining a temporal variance between the at least two temporally spaced compositions; and
      (iii) when the temporal variance falls with a predetermined temporal tolerance classifying the hydrocarbon seep as being indicative of the presence of reservoired hydrocarbons.

2. The method of claim 1, wherein step c) comprises constructing a phase envelope from the sample of hydrocarbons.

3. The method of claim 1, wherein the sample is isobaric.

4. The method of claim 1, wherein gas and oil samples are independently collected, and the gas and oil samples are recombined based on gas and oil volumetric flow rates prior to determining the fluid properties.

5. The method of claim 1, wherein the sample comprises oil, gas and combinations thereof.

6. The method of claim 1, wherein the at least two compositions comprises at least two temporally spaced isotopic compositions selected from the group consisting of isotopologues of methane, ethane, propane, butane, carbon dioxide, hydrogen sulphide, and combinations thereof.

7. The method of claim 1, wherein the sample is analysed to measure a fluid property selected from the group consisting of viscosity, gas:oil ratio, dew point, bubble point, molecular composition, isotopic composition, API gravity, density and combinations thereof.

8. The method of claim 1, further comprising the step of determining a formation volume factor for oil.

9. The method of claim 1, wherein step c) is determined in-situ, remotely or a combination thereof.

* * * * *

UNITED STATES PATENT AND TRADEMARK OFFICE
CERTIFICATE OF CORRECTION

PATENT NO. : 12,111,305 B2
APPLICATION NO. : 17/611349
DATED : October 8, 2024
INVENTOR(S) : Leslie Owuraku Baksmaty et al.

Page 1 of 1

It is certified that error appears in the above-identified patent and that said Letters Patent is hereby corrected as shown below:

In the Claims

In Column 7, Line 21, in Claim 1, after "least" insert -- two --.
In Column 7, Line 28, in Claim 1, delete "tolerance" and insert -- tolerance, --.

Signed and Sealed this
Thirty-first Day of December, 2024

Derrick Brent
*Acting Director of the United States Patent and Trademark Office*